(12) United States Patent
McCook et al.

(10) Patent No.: US 8,298,555 B2
(45) Date of Patent: *Oct. 30, 2012

(54) COLOR COSMETIC COMPOSITIONS FOR TOPICAL ANTI-AGING SKIN TREATMENT

(75) Inventors: John Patrick McCook, Frisco, TX (US); Peter Ladislaus Dorogi, Easton, PA (US); David Bruce Vasily, Bethlehem, PA (US); Deborah Lynn Lydic, Spring Hill, TN (US); David Blair Allen, Franklin, TN (US)

(73) Assignee: Discovery Partners, LLC, Frisco, TX (US)

( * ) Notice: Subject to any disclaimer, the term of this patent is extended or adjusted under 35 U.S.C. 154(b) by 145 days.

This patent is subject to a terminal disclaimer.

(21) Appl. No.: 11/809,981

(22) Filed: Jun. 4, 2007

(65) Prior Publication Data

US 2008/0299155 A1    Dec. 4, 2008

(51) Int. Cl.
*A61K 8/02* (2006.01)
*A61K 8/18* (2006.01)
*A61Q 1/02* (2006.01)
*A61Q 1/04* (2006.01)
*A61Q 1/06* (2006.01)
*A61Q 19/08* (2006.01)

(52) U.S. Cl. .............................. 424/401; 424/63; 424/64
(58) Field of Classification Search ........................ None
See application file for complete search history.

(56) References Cited

U.S. PATENT DOCUMENTS

| 2003/0095935 A1* | 5/2003 | Chaiyawat et al. | 424/63 |
| 2007/0148222 A1* | 6/2007 | Dorogi et al. | 424/450 |
| 2007/0148223 A1* | 6/2007 | Dorogi et al. | 424/450 |
| 2007/0148224 A1* | 6/2007 | Dorogi et al. | 424/450 |
| 2010/0247591 A1* | 9/2010 | Dorogi et al. | 424/401 |
| 2010/0247628 A1* | 9/2010 | Dorogi et al. | 424/450 |
| 2010/0247630 A1* | 9/2010 | Dorogi et al. | 424/450 |

OTHER PUBLICATIONS

Dragićević-Ćurić et al., "Hydrophilic Gels Containing Chlorophyllin-Loaded Liposomes: Development and Stability Evaluation," Pharmazie, vol. 60 (2005) No. 8, pp. 588-592.*

* cited by examiner

*Primary Examiner* — Yong Chong
*Assistant Examiner* — Jody Karol
(74) *Attorney, Agent, or Firm* — Louis C. Paul

(57) ABSTRACT

This invention discloses color cosmetic compositions and methods for anti-aging treatments that utilize plant-based copper antioxidant complexes.

13 Claims, No Drawings

COLOR COSMETIC COMPOSITIONS FOR TOPICAL ANTI-AGING SKIN TREATMENT

FIELD OF THE INVENTION

This invention is directed toward topical compositions and methods of use for skin treatment formulations containing plant-based antioxidant pigment complexes in color cosmetic vehicles.

BACKGROUND OF THE INVENTION

U.S. application Ser. No. 11/496,155 filed, Jul. 31, 2006, and entitled "SKIN TREATMENT COMPOSITIONS CONTAINING COPPER-PIGMENT COMPLEXES" describes therapeutic substances and methods for treating, preventing, reversing or inhibiting skin disorders. The present invention is directed to and discloses improved skin delivery systems for the copper-antioxidant pigment complexes and novel compositions containing a copper-antioxidant pigment complex combined with color cosmetic pigments and colors that deliver anti-aging benefits when applied to facial skin or lips.

SUMMARY OF THE INVENTION

In the present invention, cutaneous topical delivery of copper is carried out by binding copper with a botanical pigment.

The term "pigment", when used in conjunction with copper, covers botanical or naturally-derived chromophoric molecules, or chemically modified botanical chromophores, possessing antioxidant properties. The copper-pigment complex utilized and demonstrated herein is sodium-copper-chlorophyllin. The copper-pigment complex can also be identified as a copper-antioxidant pigment complex, a copper-plant complex, or a copper pigment antioxidant complex.

The penetration of the copper-pigment complex into the skin is enhanced with the inclusion of penetration enhancing substances. In one embodiment, skin penetration of the copper-pigment complex is enhanced by encapsulating the copper-pigment complex within liposomes. The liposomes used are submicron size, with the majority of liposomes having an average particle diameter below 350 nanometers or 0.35 microns.

The invention disclosed here is designed, in part, to deliver copper to binding sites in the skin, where it can be utilized to form enzymes and wound-healing copper-peptides: for example, for preventing, reducing and eliminating the signs and symptoms of photodamage. The present invention aims to provide copper to copper-dependent antioxidant enzymes responsible for elimination of free radicals generated in the skin by ultraviolet light, reactive oxygen forms, and microbe activity.

The disclosed method supports copper-binding enzymes and peptides active in repair and replacement of damaged connective tissue.

It is also the aim of this invention to simultaneously supply to the skin, besides copper, botanical pigments which are natural antioxidants, so as to further reduce oxidation damage.

The invention utilizes therapeutic units that consist of a copper ion metallically bound to a suitable botanical pigment. Treatment involves cutaneous application of such a copper-pigment complex in a cosmetic vehicle that simultaneously facilitates penetration of the complex into the skin and delivers a uniform coating of cosmetic color to the surface of the skin. In one embodiment of the invention, the copper-pigment complex is sodium-copper-chlorophyllin. The copper-pigment complex and its carrier may be encapsulated in a submicron liposome, with the majority of liposomes below 350 nanometers Zeta-potential average diameter, and which are disclosed here to result in increased skin penetration by the copper-pigment complex.

DETAILED DESCRIPTION OF THE INVENTION

Damage to the connective tissue proteins collagen and elastin reduces the tensile strength of connective tissue. Structural weakness of connective tissue is a likely cause of telangiectasias, produced by distension and thinning of blood vessel walls. Increased tissue blood volume is visible through the skin surface and is responsible for the appearance of diffuse redness. It is disclosed here that increased cross-linking of connective tissue proteins due to increased bioavailability of copper can 1) reduce the visibility of under-eye dark circles, 2) improve tensile strength and elasticity of skin and thereby diminish the appearance of fine lines and wrinkles, and 3) reduce the appearance of under-eye puffiness or edema.

Binding copper with an antioxidant botanical pigment imparts important additional protection against oxidative damage. The skin has intrinsic mechanisms for repair of damaged cells and macromolecules produced after oxidative injury. However, wound healing also includes the body's own production and secretion of superoxide radicals ($O_2^-$) by phagocytic cells, used to destroy invading microorganisms. Although the superoxide radical is itself not very damaging, it can react with transition metals such as ferrous iron ($Fe^{+2}$) and cuprous copper ($Cu^{+2}$) to generate the extremely reactive hydroxyl radical $OH^-$. To offset such potentially harmful side-effects copper-delivery compositions are utilized wherein copper is applied in forms that provide their own antioxidant protection: namely, copper bound with protective botanical pigments.

Elimination of the superoxides is carried out by superoxide dismutases (SODs). The predominant form of SOD in the skin is the $Cu^{+2}/Zn^{+2}$ containing dimeric form of the enzyme. Increasing the amount of copper in the skin can result in increased SOD activity, reducing skin inflammation.

The copper-antioxidant pigment complex is applied to the skin in a color cosmetic base or vehicle containing one or more penetration-enhancing ingredients. Suitable permeation enhancers include, ethoxydiglycol (also known as diethylene glycol monoethyl ether, commercially available as TRANSCUTOL from Gattefosse and TRIVALIN CG from Tri-K Industries), 1,3-butylene glycol, isopentyl diol or isoprene glycol, dimethyl isosorbide, propylene glycol, 1,2-pentane diol, propylene glycol, 2-methyl propan-2-ol, propan-2-ol, ethyl-2-hydroxypropanoate, hexan-2,5-diol, di(2-hydroxypropyl) ether, pentan-2,4-diol, acetone, polyoxyethylene(2)methyl ether, 2-hydroxypropionic acid, 2-hydroxyoctanoic acid, propan-1-ol, 1,4 dioxane, tetrahydrofuran, butan-1,4-diol, propylene glycol dipelargonate, polyoxypropylene 15 stearyl ether, octyl alcohol, polyoxyethylene ester of oleyl alcohol, oleyl alcohol, lauryl alcohol, dioctyl adipate, dicapryl adipate, diisopropyl adipate, diisopropyl sebacate, dibutyl sebacate, diethyl sebacate, dimethyl sebacate, dioctyl sebacate, dibutyl suberate, dioctyl azelate, dibenzyl sebacate, dibutyl phthalate, dibutyl azelate, ethyl myristate, dimethyl azelate, butyl myristate, dibutyl succinate, didecyl phthalate, decyl oleate, ethyl caproate, ethyl salicylate, isopropyl palmitate, ethyl laurate, 2-ethyl-hexyl pelargonate, isopropyl isostearate, butyl laurate, benzyl benzoate, butyl benzoate, hexyl laurate, ethyl caprate, ethyl caprylate, butyl stearate, benzyl salicylate, 2-hyroxyoctanoic acid, dimethyl sulphoxide, methyl sulfonyl methane (MSM), n,n-dimethyl acetamide, n,n-dimethyl formamide, 2-pyrrolidone, 1-methyl-2-pyrrolidone, 5-methyl-2-pyrrolidone, 1,5-dimethyl-2-pyrrolidone, 1-ethyl-2-pyrrolidone, phosphine oxides, sugar esters, tetrahydrofurfural alcohol, urea, diethyl-m-toluamide, 1-dodecylazacyloheptan-2-one, acetamide MEA, tetrahydropiperine, various PEG glyceryl ethers, Levomenol [(−)-6-Methyl-2-((4-methyl-3-cyclohexen-1-yl)-5-hepten-2-ol], combinations thereof, and the like.

The amount of permeation enhancer in the compositions of the present disclosure may be less than about 20% by weight of the composition. In some embodiments, it necessary to utilize the permeation enhancer in an amount of about 5% by weight of the composition. Preferred penetration enhancing ingredients include the diglycols; pentylene glycol, isopentyl glycol, 1,3-butylene glycol, 1,4-butylene glycol and ethoxydiglycol, or mixtures of these diglycols.

The copper-antioxidant pigment complex and its vehicle is delivered within a liposomal dispersion, wherein the lipid shell of the liposome consists of a phospholipid, Suitable phospholipids and/or phospholipid derivatives include, but are not limited to, lecithin, lysolecithin, phosphatidylcholine, phosphatidylethanolamine, phosphatidylinositol, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, combinations thereof, and the like.

In some embodiments, a lecithin derived from egg or soybean can be utilized as the phospholipid. Such lecithins include those commercially available as PHOSPHOLIPON® 85G, PHOSPHOLIPON® 90G, and PHOSPHOLIPON® 90H (the fully hydrogenated version of PHOSPHOLIPON® 90G) from American Lecithin Company, Oxford, Conn. Other suitable lecithins include LECINOL S-10® lecithin from Nikko Chemicals. Preferably, a vegetable-based phosphatidyl choline or soy lecithin is used to make the liposomes. Liposomes of this type can be made in situ by dissolving the copper-pigment complex in water and encapsulating the aqueous copper complex with Phospholipon 80® or Phospholipon 85G®. Lecithin of this type are obtained from the American Lecithin Company, originally manufactured by Phospholipid GmbH (Cologne, Germany) and typically contains more than 50% linoleic acid. Alternatively, the liposomes may be made using diacylglycerol-polyethyleneglycol (DAG-PEG) lipidsIns. In one embodiment of the invention, liposomes containing sodium copper chlorophyllin were made using PEG-12 glyceryldimyristate supplied by Bio-Zone Laboratories, Inc. of Pittsburgh, Calif. The aqueous liposome dispersion of the copper-antioxidant pigment complex and penetration enhancing diols are then formulated in a color cosmetic vehicle.

The invention combines four types of ingredients in the therapeutic unit; said ingredients contained in a suitable color cosmetic vehicle: copper ions, antioxidant botanical pigments, skin penetration enhancing vehicles containing certain diglycols, and lipids in the form of liposomes.

Another aspect of the invention is a method for controlled release of copper in the skin, based on suitable formulation of the pH of the therapeutic unit compared with the internal pH of the skin. In the case of sodium-copper-chlorophyllin, copper is bound to the chlorophyllin by a metallic bond and can be replaced by two protons: a more acidic environment releases the copper, slightly increasing the concentration of the free form, $Cu^{+2}$, by trace amounts. It is thereby another aspect of the invention that the therapeutic unit is formulated in a vehicle at a slightly alkaline pH: typically, a pH range of 7.2 to 7.6 gives good results. Aqueous solutions of sodium-copper-chlorophyllin complex are typically alkaline, in the pH-range 8.0-9.5 prior to any pH adjustment via acidifying agents or buffering agents. When liposomal dispersants are used to enhance skin penetration, the pH of the liposomal dispersion is adjusted to a slightly alkaline pH of 7.2-7.6 to stabilize sodium-copper-chlorophyllin.

The more acidic environment of the skin's outer mantle can enhance release of copper from the pigment complex. Encapsulation by liposomes acts as a shield against this "acid shock", resulting in deeper skin penetration, slower release, and potentially enhanced biological utilization of copper. In a "proof-of-principle" study with one human subject, increased utilization of copper was demonstrated for the liposomal system; the experiment is described in detail in the "liposome penetration enhancement study" below. This proof-of-principle study indicates that 1) the aqueous composition containing sodium-copper-chlorophyllin and diglycol penetration-enhancing agents deliver copper to the enzyme tyrosine hydroxylase situated at the base of the epidermis and 2) encapsulation of the copper-pigment complex within a liposome increases the amount of copper delivered.

A small study, on one subject, was conducted to see whether encapsulation of the sodium-copper-chlorophyllin within the liposome enhanced skin tanning, i.e., increased penetration and bioavailability of copper to the melanin-producing enzyme, tyrosine hydroxylase. The study compared treatment with 0.10% by weight sodium-copper-chlorophyllin in a treatment gel composition as described in Exhibit 2, with and without liposome encapsulation. Three areas on the back received 1.0 MED simulated solar radiation: one area had received no treatment, one area had been pre-treated with the gel without liposome and the third area was treated with the liposome gel. An expert blinded grader scored the resulting skin tanning at 10 days after irradiation, using the Degree of Tanning scale 0 to 10 (darkest). The control, untreated area showed very little tanning and was given a tanning score of 1-2; the area treated using the gel without liposome was scored as 6.0-6.5; the area treated with the liposome gel was scored as 8. These results suggest copper from the copper-pigment complex applied in a vehicle with penetration-enhancing agents reaches and is picked up by melanocytes, with and without the liposome, but that the liposome enhances penetration beyond that achievable with the penetration enhancers used.

Another aspect of the present invention is that controlled dissociation of the sodium-copper-chlorophyllin complex can occur in part because of the high stability of this complex. Normally, inorganic and organic copper salts, including copper-peptides, are not very stable with regard to binding copper. The inherent stability and lack of reactivity of sodium-copper-chlorophyllin is essential for this process to work successfully. The stability of this copper-pigment complex is displayed by exposing a sample of the material to intense pulsed light (IPL) flashes in the visible spectral range absorbed by this dye. Stability was monitored by measurement of the dye's full absorbance spectrum, since degradation of the dye would be detectable as changes in the absorbance spectrum. Even after application of ten pulses at the maximum power of the flash lamp, the absorbance spectrum of sodium-copper-chlorphyllin remained unchanged, demonstrating high thermal and light stability for this material.

In nature, many types of botanical pigments protect plants against the free radicals generated from molecular oxygen. Antioxidant pigments are essential for the survival of plants, and the pigments usually contain a metal-ion such as magnesium, zinc, or copper. Although experiments utilized sodium-copper-chlorophyllin, topical application of other botanical pigments containing metals and possessing free radical scavenging properties are utilized in this invention. A list of examples of such pigments includes carotenoids, chlorophylls, anthocyanins, betalains and phycobilins.

Bound Cu+2 ions are loaded into the liposomes as an aqueous solution of sodium-copper-chlorophyllin. Chlorophyllin itself is a highly effective antioxidant and is expected to neutralize any free radical load put on the skin due to reactions between $Cu^{+2}$, hydrogen peroxide, and ultraviolet light, or combinations of these.

In one preferred embodiment of this invention, the carrier vehicle of the copper-pigment complex is a liposomal dispersion, containing submicron size lecithin liposomes, with the majority of the liposomes falling below 350 nm or 0.35 microns average particle diameter, and typically with an average particle diameter between 150-350 nanometers (0.15-0.35 micron). The average liposome size can be measured with laser diffraction using a Malvern ZetaSizer (MalvernInstruments, Ltd., Worcestershire, UK) or similar equipment suitable for measuring dispersions of submicron size particles. Copper ions are favored to dissociate from chlorophyllin due to the acidity of the skin compared with the formulated higher pH of the composition. This release process is expectedly slowed by liposomal encapsulation. Alternatively, dissociation of the copper-pigment complex can be increased by increasing the skin temperature by optical or sonic heating; or, the release can be slowed by cooling the skin.

Because copper ions bind with many skin peptides and proteins, benefits of this type of topical treatment depend on the applied copper reaching the critical copper-binding sites. Combination of these particular liposomes, characterized by their high stability and small size, loaded with copper bound to a suitable, stable botanical pigment, and delivered within a penetration-enhancing vehicle, are essential in this invention.

The present invention provides materials and compositions that enhance cutaneous physiological functions dependent on the presence of copper. These copper-dependent functions include repair and growth of connective tissue, regulation of mitochondrial energy metabolism, formation of melanin, and reduction of free radicals. The invention discloses methodology consisting of:
1) a composition containing a non-acidic formulation of copper bound to a botanical pigment possessing antioxidant qualities, the composition thus containing a copper-botanical-antioxidant complex;
2) identification of a carrier vehicle containing penetration enhancing agents and encapsulation of the copper-pigment antioxidant complex in stable, submicron size liposomes;
3) formulating the copper-antioxidant complex therapeutic unit, consisting of steps one and two above, into a suitable color cosmetic vehicle or base, said base containing a limited amount of purified or deionized water;
4) identification of physiological copper-binding sites in the skin that modulate intrinsic aging, or aging due to sun exposure or environmental factors, the signs including pigment changes, blotchy or uneven patches, lines and wrinkles, laxity, surface roughness, vermillion age lines of the lips, and under-eye dark circles and puffiness;
5) topically applying to skin the color cosmetic composition containing the encapsulated copper-botanical-antioxidant complex therapeutic unit, to result in enhanced penetration of the complex to cutaneous copper binding sites; and,
6) simultaneously delivering skin pH-activated copper ions and plant-based antioxidant pigments to treat said skin disorders and to protect against further skin damage.

Copper ion ($Cu^{+2}$) that is metallically bound to a botanical pigment, chlorophyllin, can function as a biologically effective copper-delivery system when suitably formulated for topical application. The pigment part of the complex can function as an antioxidant in the skin, thereby reducing reactive oxygen species and skin inflammation. The list of copper-dependent enzymes that are normally active in the skin, and thereby affected, includes lysyl oxidase (cross-links collagen fibrils to form the structurally supportive collagen fibers), superoxide dismutase (active in the reduction of damaging oxygen species), tyrosine hydroxylase (important in the synthesis of melanin and the neurotransmitter norepinephrine). Other copper-containing enzymes found in the skin are cytochrome C oxidase (involved in production of the skin's high-energy metabolic substrates) and dopamine beta-hydroxylase (involved in regulation of dopamine and norepinephrine). By donating copper to enzymes and copper-dependent wound-healing peptides, via the compositions and processes disclosed in this invention all copper-dependent needs of the skin can be treated.

The importance of copper ions in skin biology is explained herein given the necessary presence of copper at catalytic sites of various enzymes, noting also its association with small peptides, such as GHK, which modulate recovery from injury. Whereas botanically-derived pigments such as chlorophylls and carotenoids have been used previously in skin care formulations for their antioxidant potential, binding copper ions with such botanical pigments, specifically to deliver copper, is new.

Neither copper-chlorophyll nor sodium-copper-chlorophyllin have ever been used commercially in products as topical treatments for chronic dermatoses or any skin disease, for the treatment of the signs and symptoms of skin aging or for the treatment of specific facial cosmetic issues such as under-eye dark circles, under-eye puffiness, and lip lines, Sodium-copper-chlorophyllin has not been used in cosmetic products in any significant way simply because the material is a dark-green pigment, even at low concentrations. For example, sodium-copper-chlorophyllin exhibits a dark-green color in water at concentrations as low as 0.05% by weight. Topical use products are typically uncolored or lightly colored with dyes to avoid staining of the skin or are colored with insoluble and non-staining inorganic pigments. Green is, of course, not a natural skin tone. This invention shows that sodium-copper-chlorophyllin within liposomes, or in an aqueous gel vehicle with water soluble penetration enhancers, will penetrate the skin. Concentrations up to 0.1% by weight for very light skin and up to 0.5% by weight for very dark skin can be used topically; that is, the liposomal dispersion of the copper complexed pigment is absorbed and is not visibly evident after application to the treatment area. This is particularly important since the physical location of the treatment areas will typically be the face. The color of the copper complexed pigment is dark green in the case of salts of copper chlorophyllin and can be further masked by incorporating the liposomal dispersion of the water-soluble copper-antioxidant pigment in a color cosmetic formulation containing one or more inorganic pigments, certified organic dyes, and synthetic or natural pearlescent pigments. Typically this color cosmetic composition would include titanium dioxide, zinc oxide, iron oxides, mica, bismuth oxychloride, D&C organic colors, and carmine or combinations of these cosmetic pigments and colors.

The present invention has discovered;
1. that the oil-soluble copper-chlorophyll or the water-soluble copper-chlorophyllin will readily penetrate intact skin;

2. that the low level of copper-chlorophyllin 0.1% by weight, a level used as a colorant in dentifrice and foods, will produce visible improvements in skin condition that include:

visible reductions in pore size and uneven skin coloring, increased tensile strength of skin, reduction in facial and lip lines and wrinkles, reduction in under-eye puffiness and dark circles, and improvement in skin smoothness and radiance; said improvements are obtained after twice daily use of sodium-copper-chlorophyllin for only 4 weeks.

The potential of sodium-copper-chlorophyllin to be a copper-delivery agent, transferring chlorophyllin-bound copper to copper-dependent enzymes in the skin, is new, as is the concept of using the pigment to reduce free radicals produced by the additional free copper load.

One such "therapeutic unit", is prepared in an embodiment of the invention that utilizes sodium-copper-chlorophyllin as the copper-pigment complex. Botanical pigments invariably possess a metal-ligand binding site: in natural chlorophyll this binding site is occupied by a magnesium atom. The water-insoluble chlorophyll is converted to the very water-soluble form, chlorophyllin, by alkaline hydrolysis that replaces chlorophyll's methyl and phytyl ester groups with a sodium ion. Copper is substituted for magnesium by treating the chlorophyll with an acid, thereby replacing the magnesium with two hydrogen ions. The protons are replaced by a cuprous copper ion ($Cu^{+2}$) by alkaline hydrolysis with a copper salt solution.

Liposomes containing sodium-copper-chlorophyllin were prepared by using high linoleic acid lecithin (Phospholipon 80® or Phospholipon 85G®) supplied by American Lecithin Company (Oxford, Conn.) or by Phospholipid GmbH (Cologne, Germany). Typical liposome formulations made using Phospholipon lecithin and sodium copper chlorophyllin are detailed below in Exhibit 1 (Formula number JPM-01-003-B; all ingredients percentages are by weight).

| Exhibit 1 Sodium Copper Chlorophyllin Liposome Concentrate Formula # JPM-01-003-B | |
|---|---|
| Ingredient | % w/w |
| Phospholipon 85 G (Phospholipid GmbH) | 10.00 |
| Sodium Copper Chlorophyllin, USP* | 5.00 |
| Hydrolite-5 (Symrise, Inc.) | 3.00 |
| Butylene Glycol | 4.00 |
| Phenoxyethanol | 0.30 |
| Deionized Water | 77.70 |

*Supplied by Seltzer Chemical Inc., Carlsbad, CA

The above liposome formula (JPM-01-03-B) is made by first combining and dissolving the butylene glycol, Hydrolite-5 (1,2-pentane diol), and phenoxyethanol in the deionized water. This mixture is heated to approximately 50° C. before adding the sodium copper chlorophyllin. This mixture is then mixed until the chlorophyllin salt is fully dissolved. The mixture is then cooled to 25-30° C. and the Phospholipon lecithin is added. The aqueous solution of sodium copper chlorophyllin and the lecithin are homogenized with a Waring® type blender, Osterizer®, Eppenbach® or Silverson® homogenizer or a similar mixer capable of high shear mixing. High shear mixing is continued at approximately 7000 rpm for approximately 15 minutes to create a uniform liposome dispersion with the average liposome particle measuring between 150-350 nanometers with the majority of the particles below 300 nm. The resulting liposomal dispersion of sodium copper chlorophyllin is a dark green, syrup-like liquid with a pH of 8.5-9.5. Buffer solution can be added to maintain the pH of the final liposome dispersion in the range of 7.5-8.5.

Liposome dispersions of the sodium copper chlorophyllin can also be made by changing the ratio of Phospholipon from the 2:1 ratio of lecithin: sodium copper chlorophyllin used in Exhibit 1 to higher or lower ratios of Phospholipon to chlorophyllin salt.

In another embodiment of the invention, the therapeutic unit of the copper-antioxidant pigment complex in the form of an aqueous liposomal concentrate of sodium copper chlorophyllin as shown in Exhibit 1 was incorporated within a lip liner pencil formulation (Formula # BGP-12-139-1; Cocoa) listed in Exhibit 2. The liposome dispersion was incorporated into the cosmetic lip liner base with a final formula percentage of 0.10% by weight sodium copper chlorophyllin. The lip liner base is hot poured into a plastic sheath or barrel which is then sealed at the top of the pencil and typically sharpened to a point at the application end of the pencil. An application end cap is placed over the application point to avoid dry-out and or smudging of the lip liner applicator. The processing of the lip liner pencil base is further described under Exhibit 2.

| Exhibit 2 Lip Liner Pencil; Formula # BGP-12-139-1; Shade; Cocoa | |
|---|---|
| INCI Name | Amount (% w/w) |
| Jojoba Esters | 25.31 |
| Pentaerythrityl Tetraisostearate | 13.18 |
| PPG-2 Myristyl Ether Propionate | 12.64 |
| Aqua | 6.05 |
| *Copernicia Cerifera* (Carnauba) Wax | 5.72 |
| Ceresin | 5.72 |
| Glycerin | 4.50 |
| Polyethylene | 4.00 |
| Hydrogenated Palm Glycerides | 2.43 |
| Hydrogenated Palm Kernel Glycerides | 2.43 |
| Hydrogenated Lecithin | 1.00 |
| Diazolidinyl Urea | 0.30 |
| Methylparaben | 0.20 |
| Lecithin | 0.20 |
| Chlorophyllin-Copper Complex | 0.10 |
| Propylparaben | 0.10 |
| Butylene Glycol | 0.08 |
| BHT | 0.06 |
| Pentylene Glycol | 0.06 |
| Phenoxyethanol | 0.01 |
| Titanium Dioxide Cl 77891 | 6.99 |
| Iron Oxides Yellow Cl 77492 | 3.84 |
| Iron Oxides Red Cl 77491 | 2.28 |
| Iron Oxides Black Cl 77499 | 1.39 |
| D & C Red #7 Calcium Salt Cl 15850:1 | 0.83 |
| Mica Cl 77019 | 0.58 |
| Total: | 100.00 |

The lip liner formula shown in Exhibit 2 is manufactured according to the following procedure:

Oil Phase

1) To a vessel add the following ingredients: Jojoba Esters, Pentaerythrityl Tetraisosteartate, PPG-2 Myristyl Ether Propionate, Copernicia Cerifera (Carnauba) Wax, Ceresin, Polyethylene, Hydrogenated Palm Glycerides, Hydrogenated Palm Kernel Glycerides. (Begin heating main vessel to 110° C. and power on the agitator once the waxes begin to melt.)

2) Once the mass in the main vessel reaches 110° C. and the ingredients in the vessel are clear and homogenous, then decrease the batch heat to 90° C.

3) Once batch reaches 90° C., slowly add Methylparaben, Propylparaben, and BHT to the batch mixing.
4) Continue mixing until the crystals are completely dissolved.
5) Add colorants (organics, inorganics, and pearls) to the batch and mix until uniform.
6) Transfer the batch to a three roll mill and mill the batch 2-3 times. Check the dispersion using two glass slides. If batch is not dispersed, then repeat step 6.
7) Once dispersion is determined successful, then weigh for loss and add the amount of oil phase needed to the main vessel.
8) Begin heating the main vessel to 85° C. Once the mass begins to melt begin mixing the batch.

Water Phase
9) Add DI Water and Glycerin to another vessel. Begin mixing and heat this batch to 85° C.
10) Sprinkle in the Lecinol S-10(Lecithin) and Diazolidinyl Urea to the water phase and thoroughly mix.

Homogenization:
1) Verify both the oil phase and water phase temperatures are 85° C.
2) Increase mixing speed of the main vessel containing the oil phase and power on the homogenizer.
3) Set homogenizer speed to (5,000-7,000 RPM) and slowly add the water phase to the oil phase. Continue mixing and homogenize until batch is homogenous.
4) Thoroughly mix the Sodium Copper Chlorophyllin Dispersion.
5) Weigh the appropriate amount of Sodium Copper Chlorophyllin Dispersion and slowly add this amount to the batch while homogenizing.
6) Once the batch is homogenous, turn homogenizer off.
7) Place mass between two glass slides: Check for uniformity and if needed droplet size.

In another embodiment of the invention, a second, lighter pink shade of lip liner containing a different mix of cosmetic pigments, pearlescent agents, and colorants (titanium dioxide, cosmetic iron oxides, D&C Red #7 Calcium salt, Mica, Bismuth Oxychloride) was developed and is shown in Exhibit 3 below:

Exhibit 3
Lip Liner Pencil; Formula # BGP-12-191-5; Shade: Nude

| INCI Name | Amount (% w/w) |
| --- | --- |
| Jojoba Esters | 25.31 |
| Pentaerythrityl Tetraisostearate | 13.18 |
| PPG-2 Myristyl Ether Propionate | 12.64 |
| Aqua | 6.05 |
| *Copernicia Cerifera* (Carnauba) Wax | 5.72 |
| Ceresin | 5.72 |
| Glycerin | 4.50 |
| Polyethylene | 4.00 |
| Hydrogenated Palm Glycerides | 2.43 |
| Hydrogenated Palm Kernel Glycerides | 2.43 |
| Hydrogenated Lecithin | 1.00 |
| Diazolidinyl Urea | 0.30 |
| Methylparaben | 0.20 |
| Lecithin | 0.20 |
| Chlorophyllin-Copper Complex | 0.10 |
| Propylparaben | 0.10 |
| Butylene Glycol | 0.08 |
| BHT | 0.06 |
| Pentylene Glycol | 0.06 |
| Phenoxyethanol | 0.01 |
| Titanium Dioxide Cl 77891 | 7.94 |
| Iron Oxides (Cl 77491, Cl 77492, Cl 77499) | 3.25 |
| D & C Red #7 Calcium Salt Cl 15850:1 | 0.80 |
| Mica Cl 77019 | 3.32 |
| Bismuth Oxychloride Cl 77000 | 0.60 |
| Total: | 100.00 |

The lip liner formula shown in Exhibit 3 is manufactured according to the following procedure:

Oil Phase
1) To a vessel add the following ingredients: Jojoba Esters, Pentaerythrityl Tetraisosteartate, PPG-2 Myristyl Ether Propionate, Copernicia Cerifera (Carnauba) Wax, Ceresin, Polyethylene, Hydrogenated Palm Glycerides, and Hydrogenated Palm Kernel Glycerides. (Begin heating main vessel to 110° C. and power on the agitator once the waxes begin to melt.)
2) Once the mass in the main vessel reaches 110° C. and the ingredients in the vessel are clear and homogenous then decrease the batch heat to 90° C.
3) Once batch reaches 90° C., slowly add Methylparaben, Propylparaben, and BHT to the batch mixing.
4) Continue mixing until the crystals are completely dissolved.
5) Add colorants (organics, inorganics, and pearls) to the batch and mix until uniform.
6) Transfer the batch to a three roll mill and mill the batch 2-3 times. Check the dispersion using two glass slides. If batch is not dispersed, then repeat step 6.
7) Once dispersion is determined successful, then weigh for loss and add the amount of oil phase needed to the main vessel.
8) Begin heating the main vessel to 85° C. Once the mass begins to melt begin mixing the batch.

Water Phase
9) Add DI Water and Glycerin to another vessel. Begin mixing and heat this batch to 85° C.
10) Sprinkle in the Lecinol S-10(Lecithin) and Diazolidinyl Urea to the water phase and thoroughly mix.

Homogenization:
1) Verify both the oil phase and water phase temperatures are 85° C.
2) Increase mixing speed of the main vessel containing the oil phase and power on the homogenizer.
3) Set homogenizer speed to (5,000-7,000 RPM) and slowly add the water phase to the oil phase. Continue mixing and homogenize until batch is homogenous.
4) Thoroughly mix the Sodium Copper Chlorophyllin Dispersion.
5) Weigh the appropriate amount of Sodium Copper Chlorophyllin Dispersion and slowly add this amount to the batch while homogenizing.
6) Once the batch is homogenous, turn homogenizer off.
7) Place mass between two glass slides: Check for uniformity and if needed droplet size.

Exhibit 2 shows a lip liner pencil base for the shade "Cocoa" which is in the brown family of shades. A wide variety of lip liner formulation shades can be produced within the same or similar base formula by adjusting the level and types of inorganic pigments, synthetic or natural pearlescent pigments and other cosmetic colorants; for example, titanium dioxide, cosmetic iron oxides, certified external Drug & Cosmetic (external D&C) colorants, pearlescent pigment and certain organic colorants allowed by U.S. or International regulations for use in lip products, and combinations thereof may be included in the formulations. Exhibit 3 shows a second lip liner base formula made with the same base materials as Exhibit 2 but the colorants used to create a final shade involve a different mixture of titanium dioxide, cosmetic iron oxides, external D&C colorant, and pearlescent pigments in each of the examples. In one case a "Cocoa" color shade is created (Exhibit 2 and in the other example shown in Exhibit 3, a pearlescent pink shade (shade name "Nude") is created.

The dark green color of the copper chlorophyllin complex used at 0.1% by weight in each of the lip liner formula examples is completely masked by the inorganic pigments, certified D&C color, and pearlescent pigments used. In this embodiment the total amount of copper-antioxidant plant pigment complex used in the formulations may range from 0.0001% by weight to 5.0% by weight; preferably from 0.001% by weight to 0.5% by weight and most preferably from 0.01% by weight to 0.20% by weight.

The total amount of cosmetic colorants used to create the final cosmetic shade and which we have discovered will completely mask the color of the copper antioxidant plant pigment complex will range from 5-30% by weight and typically range from 10-20% by weight. The types of cosmetic colorants and the range of concentration for use in a lip liner, lipstick or lip color product may include titanium dioxide, 1.0-15.0% by weight; Cosmetic Iron Oxides, 0.1-15.0% by weight; D&C dyes, 0.01-9.0% by weight; Mica, 0.01-6.0% by weight; Bismuth Oxychloride, 0.01-1.0% by weight; Carmine, 0.1-2.0% by weight, or combinations of the cosmetic colorants to create various cosmetic shades.

The ratio of copper antioxidant pigment complex to the total amount of cosmetic colorants used in the lip liner formulations can range from 1:100,000 to 1:10 and preferably between 1:1000 and 1:100 and specifically between 1:500 and 1:200.

Lip liner formulations are typically anhydrous. However, the formulations in the examples shown (Exhibits 2 & 3) contain a water phase that allows homogenization and emulsification of an aqueous liposome dispersion of a copper-antioxidant plant complex. The inclusion of a limited amount of water phase in the lip liner base formula is an important part of the overall invention. A sufficient amount of water is necessary to uniformly disperse the aqueous liposome of sodium copper chlorophyllin. However, the total amount of water must be limited to prevent the dissolved sodium copper chlorophyllin from "bleeding" through the final formulation and causing green spots or lines to form on the surface of the product. Additionally, the water content must be limited, otherwise, the molding and application properties of the final solid lip liner mass will be too soft. In practice, we have found that the water content should be limited to about 10% by weight of the total composition. In the formulation examples, 6.05% deionized water, by weight of the total composition was utilized. The total water content will vary in proportion to the amount of the aqueous liposome dispersion of the copper-antioxidant plant pigment used in the color cosmetic composition. However, typically, the total amount of water should be limited to 10% by weight or less of the total composition, for the reasons described above. In the specific examples shown in Exhibit 2 and 3, a liposome dispersion of sodium copper chlorophyllin, identical to the formula shown in Exhibit 1, is added during the final manufacturing phase of the lip liner. In the formula examples shown in Exhibit 2 & 3, 2% by weight of the 5% sodium copper chlorophyllin liposome concentrate shown in Exhibit 1 is added to the lip liner formulation to give a final concentration of 0.1% by weight sodium copper chlorophyllin in the final lip liner formula.

The lip liner compositions shown in Exhibits 2 & 3 were applied for up to 8 hours daily by 25 volunteer subjects in a monadic, eight-week controlled usage study, with visits at baseline, 4 weeks and 8 weeks of product use. The study assessed the tolerability of the test material as well as its efficacy to reduce the appearance of wrinkles at the vermillion border of the upper lip.

Subjects' skin above the upper lips was graded for objective irritation (erythema, edema, and scaling) as well as subjective irritation (burning, stinging, itching, tightness, tingling) using a four (4) point scale (0=none, 1=mild, 2=moderate, 3=severe). The clinical efficacy parameters included fine and coarse wrinkles, tactile and visual roughness, and overall photodamage and were assessed using 10 point scales where:
0=none, 1 to 3=mild, 4 to 6=moderate and 7 to 9=severe (half-points may be used). Digital photographs and silicone replicas were taken at baseline, 4 weeks and 8 weeks.

Clinical grading and instrumentation measurements were compared to baseline to test for significant differences using a paired t-test. Mean percent change from baseline and incidence of improvement were reported for all attributes. Questionnaires were tabulated and a top box analysis performed. Group analysis for each time point was performed if questionnaires were identical. All differences were considered significant at the $p \leq 0.05$ level.

The summary results of the lip liner clinical grading and the subjects' questionnaires showed statistically significant improvement in all parameters at both 4 and 8 weeks. Replica analysis showed significant improvement in both the number and size of fine lines and wrinkles at 8 weeks. The clinical and subjective results show no safety issues and a statistically significant improvement in erythema. Detailed results are shown below in Exhibits 4a, 4b, 5a, & 5b:

Summary Statistics: Lip Liner Clinical Assessments and Replica Analysis; Study No. C07-D033; 4 Weeks Vs. Baseline & 8 Weeks Vs. Baseline

| | | | | | | | | | | | 95% | |
|---|---|---|---|---|---|---|---|---|---|---|---|---|
| | | | | | | | | | | | | |
| | | N | BL | V | $\Delta$ | $\%_\Delta$ | % + | % − | $SD_\Delta$ | $SE_\Delta$ | $CI_\Delta$ | $p\Delta$ |
| Upper Lip | Erythema | 22 | 0.14 | 0.00 | −0.14 | −100.0% | 18.1% | 0.0% | 0.32 | 0.07 | (−0.28, 0.00) | 0.0555 |
| | Edema | 22 | 0.00 | 0.00 | 0.00 | — | 0.0% | 0.0% | 0.00 | 0.00 | (—, —) | — |
| | Scaling | 22 | 0.00 | 0.00 | 0.00 | — | 0.0% | 0.0% | 0.00 | 0.00 | (—, —) | — |
| | Burning | 22 | 0.00 | 0.00 | 0.00 | — | 0.0% | 0.0% | 0.00 | 0.00 | (—, —) | — |
| | Stinging | 22 | 0.00 | 0.00 | 0.00 | — | 0.0% | 0.0% | 0.00 | 0.00 | (—, —) | — |

Exhibit 4a (4 weeks)
Study C07-D033 Delta Statistics
Week 4

-continued

Exhibit 4a (4 weeks)
Study C07-D033 Delta Statistics
Week 4

|  |  | N | BL | V | Δ | %Δ | % + | % − | SD$_Δ$ | SE$_Δ$ | 95% CI$_Δ$ | pΔ |
|---|---|---|---|---|---|---|---|---|---|---|---|---|
|  | Itching | 22 | 0.00 | 0.00 | 0.00 | — | 0.0% | 0.0% | 0.00 | 0.00 | (—, —) | — |
|  | Tightness | 22 | 0.09 | 0.00 | −0.09 | −100.0% | 9.0% | 0.0% | 0.29 | 0.06 | (−0.22, 0.04) | 0.1620 |
|  | Tingling | 22 | 0.00 | 0.00 | 0.00 | — | 0.0% | 0.0% | 0.00 | 0.00 | (—, —) | — |
|  | Vertical fine wrinkles | 22 | 4.11 | 2.82 | −1.30 | −31.4% | 100.0% | 0.0% | 0.45 | 0.10 | (−1.50, −1.09) | <0.0001 |
|  | Vertical coarse wrinkles | 22 | 3.84 | 3.32 | −0.52 | −13.6% | 59.0% | 0.0% | 0.48 | 0.10 | (−0.73, −0.31) | <0.0001 |
|  | Tactile roughness | 22 | 3.02 | 1.68 | −1.34 | −44.3% | 100.0% | 0.0% | 0.50 | 0.11 | (−1.56, −1.12) | <0.0001 |
|  | Visual roughness | 22 | 3.20 | 2.11 | −1.09 | −34.0% | 100.0% | 0.0% | 0.37 | 0.08 | (−1.25, −0.93) | <0.0001 |
|  | Overall photo-damaged appearance | 22 | 4.20 | 2.73 | −1.48 | −35.1% | 100.0% | 0.0% | 0.45 | 0.10 | (−1.68, −1.28) | <0.0001 |
| Replica Analysis | Number of fine lines and wrinkles | 7 | 478.14 | 531.14 | 53.00 | 11.0% | 42.8% | 57.1% | 78.04 | 29.50 | (−19.8, −125.18) | 0.1224 |
|  | Size of fine lines and wrinkles | 7 | 70848 | 70328 | −520.1 | −0.7% | 57.1% | 42.8% | 13037 | 4927.6 | (−12577, 11537) | 0.9193 |

Exhibit 4b (8 weeks)
Study C07-D033 Delta Statistics
Week 8

|  |  | N | BL | V | Δ | %Δ | % + | % − | SD$_Δ$ | SE$_Δ$ | 95% CI$_Δ$ | pΔ |
|---|---|---|---|---|---|---|---|---|---|---|---|---|
| Upper Lip | Erythema | 22 | 0.14 | 0.00 | −0.14 | −100.0% | 18.1% | 0.0% | 0.32 | 0.07 | (−0.28, 0.00) | 0.0555 |
|  | Edema | 22 | 0.00 | 0.00 | 0.00 | — | 0.0% | 0.0% | 0.00 | 0.00 | (—, —) | — |
|  | Scaling | 22 | 0.00 | 0.00 | 0.00 | — | 0.0% | 0.0% | 0.00 | 0.00 | (—, —) | — |
|  | Burning | 22 | 0.00 | 0.00 | 0.00 | — | 0.0% | 0.0% | 0.00 | 0.00 | (—, —) | — |
|  | Stinging | 22 | 0.00 | 0.00 | 0.00 | — | 0.0% | 0.0% | 0.00 | 0.00 | (—, —) | — |
|  | Itching | 22 | 0.00 | 0.00 | 0.00 | — | 0.0% | 0.0% | 0.00 | 0.00 | (—, —) | — |
|  | Tightness | 22 | 0.09 | 0.00 | −0.09 | −100.0% | 9.0% | 0.0% | 0.29 | 0.06 | (−0.22, 0.04) | 0.1620 |
|  | Tingling | 22 | 0.00 | 0.00 | 0.00 | — | 0.0% | 0.0% | 0.00 | 0.00 | (—, —) | — |
|  | Vertical fine wrinkles | 22 | 4.11 | 2.14 | −1.98 | −48.0% | 100.0% | 0.0% | 0.84 | 0.18 | (−2.35, −1.61) | <0.0001 |
|  | Vertical coarse wrinkles | 22 | 3.84 | 3.20 | −0.64 | −16.5% | 68.1% | 0.0% | 0.49 | 0.10 | (−0.85, −0.42) | <0.0001 |
|  | Tactile roughness | 22 | 3.02 | 0.73 | −2.30 | −75.9% | 100.0% | 0.0% | 0.43 | 0.09 | (−2.48, −2.11) | <0.0001 |
|  | Visual roughness | 22 | 3.20 | 1.34 | −1.86 | −58.1% | 100.0% | 0.0% | 0.52 | 0.11 | (−2.09, −1.63) | <0.0001 |
|  | Overall photo-damaged appearance | 22 | 4.20 | 1.95 | −2.25 | −53.5% | 100.0% | 0.0% | 0.53 | 0.11 | (−2.48, −2.02) | <0.0001 |
| Replica Analysis | Number of fine lines and wrinkles | 8 | 464.38 | 371.00 | −93.38 | −20.1% | 62.5% | 37.5% | 101.58 | 35.91 | (−178.3, −8.45) | 0.0354 |
|  | Size of fine lines and wrinkles | 8 | 74622 | 61169 | −13454 | −18.0% | 87.5% | 12.5% | 15779 | 5578.8 | (−26646, −261.9) | 0.0466 |

Summary Statistics: Lip Liner Subjects' Assessments; Study No. C07-D033; 4 Weeks Vs. Baseline & 8 Weeks Vs. Baseline

| Exhibit 5a (4 weeks) Study C07-D033 Week 4 Summary | | | |
|---|---|---|---|
| Question | Top Box | Bottom Box | P-Value |
| 1. Please check the selection that best describes the overall rating of the lip liner: | 19(86.4%) | 1(4.5%) | <0.001 |
| 2. Refines skin surface | 17(77.3%) | 1(4.5%) | <0.001 |
| 3. Moisturizes lips | 18(81.8%) | 2(9.1%) | <0.001 |
| 4. Improves texture every time you wear it | 16(72.7%) | 1(4.5%) | <0.001 |
| 5. Improves condition every time you wear it | 17(77.3%) | 1(4.5%) | <0.001 |
| 6. Lips looks healthier | 18(81.8%) | 1(4.5%) | <0.001 |
| 7. Minimizes appearance of imperfections | 18(81.8%) | 1(4.5%) | <0.001 |
| 8. Smoothes lips | 20(90.9%) | 0(0%) | <0.001 |
| 9. Softens lips | 19(86.4%) | 0(0%) | <0.001 |
| 10. Conditions lips | 19(86.4%) | 0(0%) | <0.001 |
| 11. Improves lips radiance | 16(72.7%) | 1(4.5%) | <0.001 |
| 12. Improves lips clarity | 18(81.8%) | 1(4.5%) | <0.001 |
| 13. Reduces fine lines above my upper lip | 15(68.2%) | 3(13.6%) | 0.005 |
| 14. Reduces wrinkles above my upper lip | 13(59.1%) | 4(18.2%) | 0.029 |
| 15. Is gentle | 22(100%) | 0(0%) | <0.001 |
| 16. Leaves lips looking younger | 18(81.8%) | 1(4.5%) | <0.001 |
| 17. My lipstick has bled less into the fine | 18(81.8%) | 3(13.6%) | 0.001 |
| 18. Allows for smooth application of lipstick | 22(100%) | 0(0%) | <0.001 |
| 19. Lip liner feels comfortable after application. | 22(100%) | 0(0%) | <0.001 |
| 20. Lipstick feels better with use of the product. | 20(90.9%) | 1(4.5%) | <0.001 |
| 21. Support my lips natural volume | 19(86.4%) | 0(0%) | <0.001 |
| 22. Increases my lip volume (lips look and feel more plump and more full) | 16(72.7%) | 1(4.5%) | <0.001 |
| 23. The product refined the contour/shape of my lip. | 20(90.9%) | 2(9.1%) | <0.001 |
| 24. The product enhanced the contour/shape of my lip. | 21(95.5%) | 1(4.5%) | <0.001 |
| 25. Is good for everyday use | 21(95.5%) | 0(0%) | <0.001 |

| Exhibit 5b (8 weeks) Study C07-D033 Week 8 Summary | | | |
|---|---|---|---|
| Question | Top Box | Bottom Box | P-Value |
| 1. Please check the selection that best describes the overall rating of the lip liner: | 20(90.9%) | 0(0%) | <0.001 |
| 2. Refines skin surface | 20(90.9%) | 1(4.5%) | <0.001 |
| 3. Moisturizes lips | 19(86.4%) | 2(9.1%) | <0.001 |
| 4. Improves texture every time you wear it | 18(81.8%) | 3(13.6%) | 0.001 |
| 5. Improves condition every time you wear it | 18(81.8%) | 2(9.1%) | <0.001 |
| 6. Lips looks healthier | 18(81.8%) | 2(9.1%) | <0.001 |
| 7. Minimizes appearance of imperfections | 20(90.9%) | 0(0%) | <0.001 |
| 8. Smoothes lips | 21(100%) | 0(0%) | <0.001 |
| 9. Softens lips | 19(86.4%) | 2(9.1%) | <0.001 |
| 10. Conditions lips | 19(86.4%) | 2(9.1%) | <0.001 |
| 11. Improves lips radiance | 17(77.3%) | 2(9.1%) | <0.001 |
| 12. Improves lips clarity | 19(86.4%) | 1(4.5%) | <0.001 |
| 13. Reduces fine lines above my upper lip | 17(77.3%) | 3(13.6%) | 0.002 |
| 14. Reduces wrinkles above my upper lip | 15(68.2%) | 4(18.2%) | 0.012 |
| 15. Is gentle | 22(100%) | 0(0%) | <0.001 |
| 16. Leaves lips looking younger | 17(77.3%) | 2(9.1%) | <0.001 |
| 17. My lipstick has bled less into the fine | 18(81.8%) | 4(18.2%) | 0.003 |
| 18. Allows for smooth application of lipstick | 22(100%) | 0(0%) | <0.001 |
| 19. Lip liner feels comfortable after application. | 22(100%) | 0(0%) | <0.001 |
| 20. Lipstick feels better with use of the product. | 20(90.9%) | 1(4.5%) | <0.001 |
| 21. Supports my lips natural volume | 21(95.5%) | 0(0%) | <0.001 |
| 22. Increases my lip volume (lips look and feel more plump and more full) | 19(86.4%) | 1(4.5%) | <0.001 |
| 23. The product refined the contour/shape of my lip. | 18(81.8%) | 1(4.5%) | <0.001 |
| 24. The product enhanced the contour/shape of my lip. | 19(86.4%) | 1(4.5%) | <0.001 |
| 25. Is good for everyday use | 21(95.5%) | 1(4.5%) | <0.001 |

This lip liner study shows that the presence of the copper-antioxidant plant pigment complex, present in the lip liner formulas as 0.1% by weight, sodium-copper-chlorophyllin, is primarily responsible for the improvements noted above, since the lip liner formulas tested contain no other formula ingredient or combination of ingredients known to have an anti-aging treatment effect or that would demonstrate such dramatic change over 4 weeks or 8 weeks of treatment. The composition of the lip liner formulations, as listed in Exhibits 2 & 3, contain emollients, humectants, waxes, emulsifiers, preservatives, and cosmetic pigments or colors, collectively used and known to those skilled in the art of cosmetic formulation of lip pencil base formulas. With the exception of copper-antioxidant plant pigment complexes and specifically the use of sodium copper chlorophyllin, the lip liner base formulas, as such, do not contain any cosmeceutical or pharmaceutical skin anti-aging agent or agents or ingredients recognized as exerting a significant anti-aging effect on photo-damage associated with the lips.

The use of copper-antioxidant plant pigment complexes and specifically the use of sodium copper chlorophyllin as an anti-aging treatment is not limited to the example lip liner composition but is meant to apply to lip care, lip color, or lip treatment products in general, including, but not limited to lip liner, lip stick, lip gloss, lip pens, lip pencils and lip jelly, Copper-antioxidant plant pigment complexes and specifically, sodium copper chlorophyllin, have not been recognized as having any utility in lip care or lip treatment products. The discovery that copper-antioxidant plant pigment complexes can be used in cosmetic lip care formulations to significantly treat, improve, or reverse the signs and symptoms of photo-damage or photo-aging, or aging of the lips, is truly novel and unexpected. Given that the invention has demonstrated the improvement of existing signs of aging present on the lips, it is further expected that the lip care formulations thus described may be used to prevent further damage.

In another embodiment of the invention, the copper-antioxidant pigment complex was incorporated within an under-eye concealer formulation (Formula No. SAD-10-37-1) listed in Exhibit 6 below. The copper-antioxidant pigment complex used was sodium copper chlorophyllin. This copper chlorophyllin salt was first dissolved in water and processed into a liposome dispersion as was described in Exhibit 1. The liposome dispersion was incorporated into the cosmetic under-eye concealer base with a final formula percentage of 0.10% by weight sodium copper chlorophyllin. The under-eye concealer base is hot poured into a plastic sheath or barrel and capped. The under-eye concealer base is thus in the form of a solid stick contained in a cylindrical or oval tube with a swivel or other mechanism that allows the under-eye concealer base to be extruded above the tube or barrel for application of the cosmetic stick to the area around the eye; the so-called periorbital area of the face. The processing of the under-eye concealer base is further described under Exhibit 6.

Exhibit 6
Under-Eye Concealer; Formula No. SAD-10-37-1

| INCI Name | Amount (% w/w) |
|---|---|
| Phenyl Trimethicone | 26.51 |
| Octyldodecanol | 8.02 |
| Caprylic/Capric Triglyceride | 7.08 |
| Isononyl Isononanoate | 6.06 |
| Aqua | 5.46 |
| *Euphorbia Cerifera* (Candelilla) Wax | 4.78 |
| Polyethylene | 4.13 |
| *Copernicia Cerifera* (Carnauba) Wax | 4.13 |
| Glycerin | 3.60 |
| Polymethyl Methacrylate | 2.75 |
| Synthetic Wax (paraffin) | 1.64 |
| Hydrogenated Palm Glycerides | 1.41 |
| Hydrogenated Palm Kernel Glycerides | 1.41 |
| Cholesteryl, Behenyl, Octyldodecyl Lauroyl Glutamate | 0.80 |
| Silica | 0.80 |
| Hydrogenated Lecithin | 0.80 |
| Dimethicone | 0.40 |
| Trimethylsiloxysilicate | 0.40 |
| PEG 40 Hyrogenated castor oil | 0.31 |
| PPG 26 Buteth 26 | 0.31 |
| Diazolidinyl Urea | 0.30 |
| Lecithin | 0.20 |
| Methylparaben | 0.20 |
| Propylparaben | 0.10 |
| Chlorophyllin-Copper Complex | 0.10 |
| Butylene Glycol | 0.08 |
| Pentylene Glycol | 0.06 |
| BHT | 0.06 |
| Butylparaben | 0.05 |
| Citric Acid | 0.03 |
| Phenoxyethanol | 0.01 |
| Titanium Dioxide Cl 77891 | 16.09 |
| Iron Oxides Red Cl 77491 | 1.05 |
| Iron Oxides Yellow Cl 77492 | 0.86 |
| Total: | 100.00 |

The under-eye concealer formula shown above in Exhibit 6 is manufactured according to the following procedure:

1) To a vessel add the following ingredients: Octyldodecanol, Caprylic/Capric Triglyceride, Isononyl Isononanoate, Euphorbia Cerifera (Candelilla) Wax, Polyethylene, Copernicia Cerifera (Carnauba) Wax, Synthetic Wax (paraffin), Hydrogenated Palm Glycerides, Hydrogenated Palm Kernel Glycerides, Cholesteryl, Behenyl, Octyldodecyl Lauroyl Glutamate, (Begin heating main vessel to 110° C. and power on the agitator once the waxes begin to melt.)

2) Once the mass in the main vessel has reached 110° C. and the ingredients in the vessel are clear and homogenous, then decrease the batch heat to 95° C.

3) Once batch reaches 95° C., add the Phenyl Trimethicone, Dimethicone/TMS and Solubilisant (PEG 40 Hyrogenated castor oil/PPG 26 Buteth 26).

4) Decrease batch temperature to 90° C. While mixing the batch add Methylparaben, Propylparaben, Butylparaben, Citric Acid, and BHT. Continue mixing until the crystals are completely dissolved.

5) Next, slowly add the Polymethyl Methacrylate and Silica to the batch. Continue mixing the batch until homogenous.

6) Add colorants to the batch and mix until uniform.

7) Transfer mass to a three roll mill and mill the batch 2-3 times. Check the dispersion using two glass slides. If batch is not dispersed, then repeat step 7.

8) Once dispersion is determined successful, then weigh for loss and add the amount of oil phase needed to the main vessel.

9) Begin heating the main vessel to 85° C. Once the mass begins to melt begin mixing the batch.

Water Phase

10) Add DI Water and Glycerin to another vessel. Begin mixing and heat this batch to 85° C.

11) Sprinkle in the Lecinol S-10(Lecithin) and Diazolidinyl Urea to the water phase and thoroughly mix.

Homogenization:

1) Verify both the oil phase and water phase temperatures are 85° C.
2) Increase mixing speed of the main vessel containing the oil phase and power on the homogenizer.
3) Set homogenizer speed to (5,000-7,000 RPM) and slowly add the water phase to the oil phase. Continue mixing and homogenize until batch is homogenous.
4) Thoroughly mix the Sodium Copper Chlorophyllin Dispersion.
5) Weigh the appropriate amount of Sodium Copper Chlorophyllin Dispersion and slowly add this amount to the batch while homogenizing.
6) Once the batch is homogenous, turn homogenizer off.
7) Place mass between two glass slides: Check for uniformity and if needed droplet size.

Exhibit 6 above shows an under-eye concealer formula that was created as a neutral shade that would be acceptable for a wide variety of human skin types based on the typical natural pigmentation of various human racial characteristics. Alternative shades that are lighter or darker or that have more or less red or yellow undertones or hues may be formulated without losing any of the anti-aging skin treatment characteristics of the invention. A variety of different shades that would match different skin colors and tones would be formulated by adjusting the level and type of cosmetic pigments; for example, titanium dioxide and cosmetic iron oxides or other cosmetic pigments and dyes known to those skilled in the art.

The dark green color of the copper chlorophyllin complex used at 0.1% by weight in the under-eye concealer formulation is completely masked by the cosmetic inorganic pigments used in this example. In this embodiment the total amount of copper-antioxidant plant pigment complex used in the formulations may range from 0.0001% by weight to 5.0% by weight; preferably from 0.001% by weight to 0.5% by weight and most preferably from 0.01% by weight to 0.20% by weight of the total composition.

The total amount of cosmetic pigments and colorants used to create the final cosmetic shade and which are disclosed herein will completely mask the color of the copper antioxidant plant pigment complex and will range from 5-30% by weight and typically range from 8-20% by weight of the total composition. The types of cosmetic colorants and the ratio of copper antioxidant pigment complex to the total amount of cosmetic pigments and colorants used in the under-eye concealer may range from 1:100,000 to 1:10 and preferably between 1:1000 and 1:100 and specifically between 1:500 and 1:200.

Under-eye concealer formulations can be emulsions, suspensions or anhydrous dispersions of cosmetic pigments and colorants. The under-eye concealer formulation example shown in Exhibit 6 is a high oil content water-in-oil emulsion with a low water content (5.46% by weight). The low water content is sufficient to disperse and emulsify the sodium copper chlorophyllin liposome but low enough to prevent the water-soluble copper chlorophyllin salt from leaching, bleeding, or otherwise migrating to the surface of the final under-eye concealer composition. The inclusion of a limited amount of water phase in the under-eye concealer base formula is an important part of the overall invention. A sufficient amount of water is necessary to uniformly disperse the aqueous liposome of sodium copper chlorophyllin. However, the total amount of water must be limited to prevent the dissolved sodium copper chlorophyllin from "bleeding" or migrating through the final formulation and causing green spots or lines to form on the surface of the product. Additionally, the water content must be limited, otherwise, the molding and application properties of the final solid concealer mass will be too soft to apply properly from the applicator package. In practice, we have found that the water content should be limited to about 10% by weight of the total composition. In the formulation example, 5.46% deionized water, by weight of the total composition was utilized. The total water content will vary in proportion to the amount of the aqueous liposome dispersion of the copper-antioxidant plant pigment used in the color cosmetic composition. However, typically, the total amount of water should be limited to 10% by weight or less of the total composition for the reasons described above.

Although the example shown in Exhibit 6 is an under-eye concealer, other embodiments of the invention could be in the form of eye liner, eye shadow, liquid or solid foundation or facial bronzer.

The under-eye concealer formula, as shown above in Exhibit 6, was also used to evaluate the safety and efficacy of a copper-antioxidant plant complex composition, and, specifically, sodium copper chlorophyllin, in an 8 week controlled usage study among 25 volunteers. The volunteer subjects used the product twice daily over the course of the 8 week study and were visually assessed for safety and efficacy by a trained clinician. Additionally, digital photographs were taken at baseline, 4 weeks and 8 weeks and subjects completed a self-assessment questionnaire at these time points. Clinical Grading (visual assessment) was performed to evaluate photodamage, skin condition, and skin textural changes on each side of the face at baseline, 4 weeks and 8 weeks, and used a 10 point grading scale for the following items:
 fine wrinkles in the under-eye area (0=none, 9=severe)
 coarse wrinkles in the under-eye area (0=none, 9=severe)
 under-eye puffiness (0=none, 9=severe)
 under-eye dark circles (0=none, 9=severe)
 visual roughness/dryness, under-eye area (0=smooth, 9=rough)
 skin laxity/overall photodamage, under-eye area (0=firm/elastic, 9=loose) Safety of the under-eye concealer was graded on a 4 point scale (0=none, 1=mild, 2=moderate, 3=severe) and was used to judge
 objective irritation (erythema, edema and scaling/peeling) subjective irritation (burning, stinging, itching, tightness, dryness)

Scores for clinical grading, all parameters, were statistically compared to baseline using a paired t-test at the $p \leq 0.05$ significance level. Mean percent change from baseline and incidence of positive responders was reported for all attributes. Questionnaires were tabulated and a top-box analysis was performed. The summary results of the under-eye concealer clinical grading and the subjects questionnaires (Clinical Study C07-D032) are shown below in Exhibits 7a, 7b & 8a, 8b.

Summary Statistics Under-Eye Concealer Clinical Assessment; Study No. C07-D032; 4 Weeks Vs. Baseline & 8 Weeks Vs. Baseline Exhibit 7a (4 weeks)
C07-C032 Results
Statistical Results-Week 4

| | | N | Incidence Increase | Incidence Decrease | Mean(BL) | Mean(W4) | Mean (W4 − BL) | SD (W4 − BL) | 95% CI (W4 − BL) | p-value (W4 − BL) |
|---|---|---|---|---|---|---|---|---|---|---|
| Fine Wrinkles | Average Under Eye | 23 | 0.0% | 65.2% | 2.84 | 2.54 | −0.29 | 0.27 | (−0.41, −0.18) | <0.0001 |
| | Left Under Eye | 23 | 0.0% | 56.5% | 2.91 | 2.59 | −0.33 | 0.32 | (−0.47, −0.19) | <0.0001 |
| | Right Under Eye | 23 | 0.0% | 47.8% | 2.76 | 2.50 | −0.26 | 0.30 | (−0.39, −0.13) | 0.0003 |
| Coarse Wrinkles | Average Under Eye | 23 | 0.0% | 17.3% | 0.73 | 0.66 | −0.07 | 0.15 | (−0.13, 0.00) | 0.0556 |
| | Left Under Eye | 23 | 0.0% | 8.6% | 0.65 | 0.59 | −0.07 | 0.23 | (−0.16, 0.03) | 0.1855 |
| | Right Under Eye | 23 | 0.0% | 8.6% | 0.80 | 0.74 | −0.07 | 0.23 | (−0.16, 0.03) | 0.1855 |
| Puffiness (sub-group only) | Average Under Eye | 13 | 7.6% | 161.5% | 3.02 | 2.48 | −0.54 | 0.59 | (−0.90, −0.18) | 0.0067 |
| | Left Under Eye | 12 | 0.0% | 150.0% | 2.54 | 2.04 | −0.50 | 0.71 | (−0.95, −0.05) | 0.0322 |
| | Right Under Eye | 13 | 7.6% | 161.5% | 3.42 | 2.85 | −0.58 | 0.57 | (−0.92, −0.23) | 0.0034 |
| Dark Circles | Average Under Eye | 23 | 0.0% | 30.4% | 3.11 | 3.02 | −0.09 | 0.14 | (−0.15, −0.03) | 0.0080 |
| | Left Under Eye | 23 | 0.0% | 26.0% | 3.46 | 3.33 | −0.13 | 0.22 | (−0.23, −0.03) | 0.0107 |
| | Right Under Eye | 23 | 4.3% | 13.0% | 2.76 | 2.72 | −0.04 | 0.21 | (−0.13, −0.05) | 0.3281 |
| Visual Roughness/Dryness | Average Under Eye | 23 | 0.0% | 100.0% | 2.30 | 0.28 | −2.02 | 0.76 | (−2.35, −1.69) | <0.0001 |
| | Left Under Eye | 23 | 0.0% | 100.0% | 2.33 | 0.30 | −2.02 | 0.75 | (−2.34, −1.70) | <0.0001 |
| | Right Under Eye | 23 | 0.0% | 95.6% | 2.28 | 0.26 | −2.02 | 0.80 | (−2.37, −1.67) | <0.0001 |
| Skin Laxity/Overall Photodamage | Average Under Eye | 23 | 0.0% | 60.8% | 3.12 | 2.77 | −0.35 | 0.32 | (−0.49, −0.21) | <0.0001 |

Exhibit 7a (4 weeks) C07-C032 Results Statistical Results-Week 4

|  |  | N | Incidence Increase | Incidence Decrease | Mean(BL) | Mean(W4) | Mean (W4 − BL) | SD (W4 − BL) | 95% CI (W4 − BL) | p-value (W4 − BL) |
|---|---|---|---|---|---|---|---|---|---|---|
|  | Left Under Eye | 23 | 0.0% | 60.8% | 3.13 | 2.78 | −0.35 | 0.32 | (−0.49, −0.21) | <0.0001 |
|  | Right Under Eye | 23 | 0.0% | 60.8% | 3.11 | 2.76 | −0.35 | 0.32 | (−0.49, −0.21) | <0.0001 |

Subjects 001, 008, 015, 016, 018, 019, 020, 022, 023, 024, 025 do not qualify for left side puffiness due to a score of 0 at baseline.

Subjects 008, 015, 016, 018, 019, 020, 022, 023, 024, 025 do not qualify for right side puffiness due to a score of 0 at baseline.

Exhibit 7b (8 weeks) C07-C032 Results Statistical Results-Week 8

|  |  | N | Incedence Increase | Incidence Decrease | Mean(BL) | Mean(W8) | Mean (W8 − BL) | SD (W8 − BL) | 95% CI (W8 − BL) | p-value (W8 − BL) |
|---|---|---|---|---|---|---|---|---|---|---|
| Fine Wrinkles | Average Under Eye | 23 | 0.0% | 82.6% | 2.84 | 2.29 | −0.54 | 0.33 | (−0.69, −0.40) | <0.0001 |
|  | Left Under Eye | 23 | 0.0% | 78.2% | 2.91 | 2.35 | −0.57 | 0.38 | (−0.73, −0.40) | <0.0001 |
|  | Right Under Eye | 23 | 0.0% | 73.9% | 2.76 | 2.24 | −0.52 | 0.41 | (−0.70, −0.34) | <0.0001 |
| Coarse Wrinkles | Average Under Eye | 23 | 0.0% | 21.7% | 0.73 | 0.61 | −0.12 | 0.26 | (−0.23, −0.01) | 0.0379 |
|  | Left Under Eye | 23 | 0.0% | 8.6% | 0.65 | 0.59 | −0.07 | 0.23 | (−0.16, 0.03) | 0.1855 |
|  | Right Under Eye | 23 | 0.0% | 13.0% | 0.80 | 0.63 | −0.17 | 0.49 | (−0.39, 0.04) | 0.1034 |
| Puffines (sub-group only) | Average Under Eye | 13 | 0.0% | 176.9% | 3.02 | 1.90 | −1.12 | 0.94 | (−1.69, −0.54) | 0.0011 |
|  | Left Under Eye | 12 | 0.0% | 166.6% | 2.54 | 1.46 | −1.08 | 1.06 | (−1.76, −0.41) | 0.0046 |
|  | Right Under Eye | 13 | 0.0% | 169.2% | 3.42 | 2.23 | −1.19 | 0.97 | (−1.78, −0.61) | 0.0008 |
| Dark Circles | Average Under Eye | 23 | 4.3% | 82.6% | 3.11 | 2.77 | −0.34 | 0.33 | (−0.48, −0.20) | <0.0001 |
|  | Left Under Eye | 23 | 0.0% | 69.5% | 3.46 | 3.04 | −0.41 | 0.33 | (−0.55, −0.27) | <0.0001 |
|  | Right Under Eye | 23 | 4.3% | 52.1% | 2.76 | 2.50 | −0.26 | 0.45 | (−0.46, −0.07) | 0.0107 |
| Visual Roughness/Dryness | Average Under Eye | 23 | 0.0% | 100.0% | 2.30 | 0.00 | −2.30 | 0.91 | (−2.70, −1.91) | <0.0001 |
|  | Left Under Eye | 23 | 0.0% | 100.0% | 2.33 | 0.00 | −2.33 | 0.87 | (−2.70, −1.95) | <0.0001 |
|  | Right Under Eye | 23 | 0.0% | 95.6% | 2.28 | 0.00 | −2.28 | 0.96 | (−2.70, −1.87) | <0.0001 |
| Skin Laxity/Overall Photodamage | Average Under Eye | 23 | 0.0% | 73.9% | 3.12 | 2.51 | −0.61 | 0.52 | (−0.83, −0.39) | <0.0001 |

-continued

Exhibit 7b (8 weeks)
C07-C032 Results
Statistical Results-Week 8

| | | N | Incedence Increase | Incidence Decrease | Mean(BL) | Mean(W8) | Mean (W8 − BL) | SD (W8 − BL) | 95% CI (W8 − BL) | p-value (W8 − BL) |
|---|---|---|---|---|---|---|---|---|---|---|
| | Left Under Eye | 23 | 0.0% | 73.9% | 3.13 | 2.52 | −0.61 | 0.52 | (−0.83, −0.38) | <0.0001 |
| | Right Under Eye | 23 | 0.0% | 73.9% | 3.11 | 2.50 | −0.61 | 0.52 | (−0.83, −0.38) | <0.0001 |

Subjects 001, 008, 015, 016, 018, 019, 020, 022, 023, 024, 025 do not qualify for left side puffiness due to a score of 0 at baseline.
Subjects 008, 015, 016, 018, 019, 020, 022, 023, 024, 025, do not qualify for right side puffiness due to a score of 0 at baseline.

Summary Statistics Under-Eye Concealer, Subjects' Assessments; Study No. C07-D032; 4 Weeks Vs. Baseline & 8 Weeks Vs. Baseline Exhibit 8a (4 weeks)
Study C07-C032 Summary Self-Assessment Week 4

| Question | Top Box | Bottom Box | P-Value |
|---|---|---|---|
| The product relieved my under-eye dryness and/or roughness. | 13(56.5%) | 2(8.7%) | 0.005 |
| The product provided my under-eye skin with instant moisture. | 19(82.6%) | 0(0%) | <0.001 |
| Right after application my under-eye lines and wrinkles appear less prominent. | 16(69.6%) | 2(8.7%) | <0.001 |
| The product left my under eye skin feeling softer. | 19(82.6%) | 1(4.3%) | <0.001 |
| The product left my under eye skin feeling smoother and more supple. | 15(65.2%) | 1(4.3%) | <0.001 |
| The product reduced the appearance of under eye fine lines. | 11(47.8%) | 3(13%) | 0.033 |
| The product improved my under-eye firmness. | 9(39.1%) | 4(17.4%) | 0.166 |
| The product made my under eye skin appear fit and resilient. | 7(30.4%) | 4(17.4%) | 0.366 |
| The product made my under eye skin look younger. | 8(34.8%) | 5(21.7%) | 0.405 |
| The product restored a radiant youthful tone to my under eye skin. | 6(26.1%) | 5(21.7%) | 0.763 |
| The product minimizes the appearance of under eye puffiness. | 4(33.3%) | 2(16.7%) | 0.414 |
| The product helps reduce the appearance of under eye dark circles. | 13(56.5%) | 4(17.4%) | 0.029 |

Exhibit 8b (8 weeks)
Study C07-C032 Self-Assessment Week 8
Treatment A

| Question | Top Box | Bottom Box | P-Value |
|---|---|---|---|
| The product relieved my under-eye dryness and/or roughness. | 14(60.9%) | 1(4.3%) | <0.001 |
| The product provided my under-eye skin with instant moisture. | 19(82.6%) | 0(0%) | <0.001 |
| Right after application my under-eye lines and wrinkles appear less prominent. | 16(69.6%) | 3(13%) | 0.003 |
| The product left my under eye skin feeling softer. | 20(87%) | 1(4.3%) | <0.001 |
| The product left my under eye skin feeling smoother and more supple. | 19(82.6%) | 1(4.3%) | <0.001 |
| The product reduced the appearance of under eye fine lines. | 13(56.5%) | 3(13%) | 0.012 |
| The product improved my under-eye firmness. | 8(34.8%) | 3(13%) | 0.132 |
| The product made my under eye skin appear fit and resilient. | 9(39.1%) | 5(21.7%) | 0.285 |
| The product made my under eye skin look younger. | 11(47.8%) | 2(8.7%) | 0.013 |
| The product restored a radiant youthful tone to my under eye skin. | 11(47.8%) | 4(17.4%) | 0.071 |
| The product minimizes the appearance of under eye puffiness. | 11(47.8%) | 3(13%) | 0.033 |
| The product helps reduce the appearance of under eye dark circles. | 15(65.2%) | 5(21.7%) | 0.025 |

Statistical analysis of the clinical assessment and Subjects' assessment scores of the under-eye concealer performance show highly significant improvement in all parameters related to photo-damage or photo-aging of the under-eye and periorbital area at both the 4 week and 8 week measurement points. In particular, improvements in skin laxity and overall photodamage, fine lines and course wrinkles, and roughness and dryness are noted by both the clinical assessment and subjects' self-assessment. Additionally, highly significant improvement in both under-eye dark circles and puffiness were recorded. The aforementioned improvements are shown as the average improvement at 4 weeks or 8 weeks when compared to baseline as judged by the clinician or as rated by the subjects at 4 weeks and 8 weeks.

The above reported study establishes that the presence of the copper-antioxidant plant pigment complex in the under-eye concealer formula, as 0.1% by weight sodium copper chlorophyllin, is primarily responsible for the improvements noted above since the under-eye concealer formula tested contains no other formula ingredient or combination of ingredients recognized as an anti-aging active or that could demonstrate such dramatic change over 4 weeks or 8 weeks of treatment.

The composition of the under-eye concealer formulation, as listed in Exhibit 6, contains emollients, humectants, waxes, emulsifiers, preservatives, and cosmetic pigments, collectively used and known to those skilled in the art of cosmetic formulation of concealer formulas. With the exception of sodium copper chlorophyllin, as embodied in this invention, the under-eye concealer formula, as such, does not contain any other cosmeceutical or pharmaceutical skin anti-aging agent or agents or ingredients recognized as exerting a significant anti-aging effect on photo-damaged skin. The anti-aging use of copper-antioxidant plant pigment complexes and specifically the use of sodium copper chlorophyllin in under-eye concealer would also extend to other facial cosmetic products, including, but not limited to, liquid or solid foundation, bronzer, eye liner, and eye shadow formulations.

Copper-antioxidant plant pigment complexes and specifically, sodium copper chlorophyllin, have not been recognized as having any utility in anti-aging facial treatment products and particularly cosmetic facial products containing cosmetic pigments.

This invention discloses that copper-antioxidant plant pigment complexes can be used in cosmetic facial formulations, and specifically, under-eye concealer formulations to significantly treat, improve, or reverse the signs and symptoms of photo-damage or photo-aging, under-eye dark circles, under-eye puffiness, or any combinations thereof. Since invention described has demonstrated the improvement of existing signs of aging present on skin, particularly facial skin or photodamaged skin, it has established that the cosmetic skin care formulations thus described can be used to prevent further damage. In another embodiment of the invention, the cosmetic facial treatment formulations containing a copper-antioxidant pigment complex can be enhanced by the inclusion of one or more, sunscreen agent, skin lightening agent, anti-inflammatory agent, or other anti-aging cosmeceutical, nutriceutical or pharmaceutical agent to enhance the treatment, improvement, or prevention of photo-damaged skin, under-eye dark circles and under-eye puffiness.

What is claimed is:

1. A therapeutic color cosmetic composition for topical application to human skin or lips showing signs or symptoms of aging wherein the color cosmetic composition has a pH of from about 7.2 to about 7.6 and consists essentially of:
    a) a safe and effective amount of a liposome dispersion having a pH of from 7.5 to 8.5, said liposome dispersion consisting essentially of submicron liposomal therapeutic units, each of said therapeutic units having a lipid shell and containing
        i) an aqueous, non-acidic solution of a water-soluble botanical copper-antioxidant complex, and
        ii) at least one skin penetration-enhancing ingredient, and
    b) a solid, semi-solid or liquid color cosmetic vehicle containing at least two cosmetic colorants selected from the group consisting of inorganic pigments, organic colorants, and synthetic or natural pearlescent pigments.

2. The composition of claim 1 wherein
    a) the water-soluble botanical copper-antioxidant complex is a sodium copper chlorophyllin complex at a concentration in the range of 0.001% to 0.2% by weight of the composition,
    b) the lipid shell is comprised of one or more phospholipids and/or phospholipid derivatives selected from the group consisting of lecithin, lysolecithin, phosphatidylcholine, phosphatidylethanolamine, phosphatidylinositol, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, diacylglycerol-polyethyleneglycol lipids,
    c) the at least one skin penetration-enhancing ingredient is selected from the group consisting of 1,2-pentane diol, isopentyl glycol, 1,3-butylene glycol, 1,4-butylene glycol, and ethoxydiglycol and mixtures thereof, and
    d) the at least two cosmetic colorants are selected from the group consisting of titanium dioxide, iron oxide, mica, bismuth oxychloride, external D&C colorants, and carmine.

3. The composition of claim 2 wherein the lipid shell is comprised of one or more of (i) lecithin derived from soybean, (ii) lecithin derived from egg, (iii) vegetable-based phosphatidylcholine, or (iv) diacylglycerol-polyethyleneglycol lipids.

4. The composition of claim 1 wherein the submicron liposomal therapeutic units are formed by the steps of:
    a) creating a mixture by combining and dissolving in deionized water
        a skin penetration-enhancing ingredient selected from the group consisting of 1,2-pentane diol, isopentyl glycol, 1,3-butylene glycol, 1,4-butylene glycol, and ethoxydiglycol and mixtures thereof
    b) heating the mixture from step (a) to about 50° C., adding a botanical copper-antioxidant complex, and mixing until the complex is dissolved;
    c) cooling the mixture from step (b) to about 25° C. to 30° C. and then adding a phospholipid selected from the group consisting of (i) lecithin derived from soybean, (ii) lecithin derived from egg, (iii) vegetable-based phosphatidylcholine and (iv) diacylglycerol-polyethyleneglycol lipids;
    d) homogenizing the mixture from step (c) until forming a uniform dispersion of submicron liposomal therapeutic units, each of said therapeutic units having an average diameter of from about 150 nanometers to about 350 nanometers, and the uniform dispersion having a pH of from about 8.0 to about 9.5; and
    e) adding buffer to the uniform dispersion of submicron liposomal therapeutic units from step (d) to obtain a final liposome dispersion having a pH from 7.5 to 8.5.

5. An anti-aging cosmetic lip treatment composition consisting essentially of:
    a) a liposome dispersion of an aqueous, non-acidic solution of sodium copper chlorophyllin having a pH of from 7.5 to 8.5, said dispersion consisting essentially of submicron liposomal therapeutic units, each of said therapeutic units having a lipid shell and containing an aqueous, non-acidic solution of sodium copper chlorophyllin complex and at least one skin penetration-enhancing ingredient wherein the amount of sodium copper chlorophyllin is 0.01 to 0.2%, by weight, based on the weight of the composition;
b) water at a concentration of from 0.5% to 10.0% by weight of the total composition;
c) a solid, semi-solid or liquid color cosmetic vehicle comprising
   i) at least one non-therapeutic cosmetic ingredient selected from the group consisting of cosmetic waxes, emollients, preservatives, emulsifiers, color extenders, and processing aids, and
   ii) at least two cosmetic pigments and/or colorants selected from the group consisting of iron oxide, external D&C colorants, carmine, titanium dioxide, mica, and bismuth oxychloride, a1 wherein said cosmetic pigments and/or colorants comprise 5.0% to 90% by weight of the composition.

6. An anti-aging cosmetic facial treatment composition consisting essentially of:
a) a liposome dispersion of an aqueous, non-acidic solution of sodium copper chlorophyllin having a pH of from 7.5 to 8.5, said dispersion consisting essentially of submicron liposomal therapeutic units, each of said therapeutic units having a lipid shell and containing an aqueous, non-acidic solution of sodium copper chlorophyllin complex and at least one skin penetration-enhancing ingredient, wherein the amount of sodium copper chlorophyllin is 0.01 to 0.2%, by weight, based on the weight of the composition;
b) water at a concentration of from about 0.5% to about 10.0% by weight of the composition;
c) a solid, semi-solid or liquid color cosmetic vehicle comprising
   i) at least one non-therapeutic cosmetic ingredient selected from the group consisting of cosmetic waxes, emollients, preservatives, emulsifiers, color extenders, and processing aids, and
   ii) at least two cosmetic pigments and/or colorants selected from the group consisting of iron oxides, external D&C colorants, carmine, titanium dioxides, micas, and bismuth oxychloride, wherein said cosmetic pigments and/or colorants comprise 5.0% to 90% by weight of the composition.

7. The composition of claim 2 further comprising at least one topical anti-aging treatment material selected from the group consisting of peptides, sunscreens, isoflavones, flavenoids, isoprenoids, quinones, carotenoids, retinoids, and metalloprotease enzyme inhibitors.

8. An anti-aging cosmetic lip treatment composition according to claim 5 in the form of a lipstick, a lip pencil, a lip gloss, a lip liner or a lip protector.

9. An anti-aging facial cosmetic treatment composition according to claim 6 in the form of a cream concealer, a concealer stick, a concealer pencil, a concealer powder, an eye liner, an eye shadow or a facial foundation.

10. An anti-aging lipstick, lip pencil or lip liner according to claim 8 made by a hot pour process.

11. An anti-aging eye liner, eye pencil, concealer stick, or concealer pencil according to claim 9 made by a hot pour process.

12. The therapeutic color cosmetic composition of claim 1 wherein the submicron liposomal therapeutic dispersion includes a preservative selected from phenoxyethanol and methylparaben.

13. The composition of claim 4 wherein a preservative selected from phenoxy ethanol and methylparaben is combined with the skin-penetration enhancing agent of the mixture of step a).

* * * * *